(12) United States Patent
Decoux et al.

(10) Patent No.: US 9,223,293 B2
(45) Date of Patent: Dec. 29, 2015

(54) METHOD AND SYSTEM FOR AUTHENTICATING A TIMEPIECE

(71) Applicant: SICPA HOLDING SA, Prilly (CH)

(72) Inventors: Eric Decoux, Vevey (CH); Cecile Laporte, Yverdon-les-Bains (CH); Andrea Callegari, Chavannes-pres-Renens (CH)

(73) Assignee: SICPA HOLDING SA, Prilly (CH)

( * ) Notice: Subject to any disclaimer, the term of this patent is extended or adjusted under 35 U.S.C. 154(b) by 149 days.

(21) Appl. No.: 14/103,302

(22) Filed: Dec. 11, 2013

(65) Prior Publication Data

US 2014/0160904 A1  Jun. 12, 2014

Related U.S. Application Data

(60) Provisional application No. 61/735,785, filed on Dec. 11, 2012.

(30) Foreign Application Priority Data

Feb. 5, 2013  (WO) ................. PCT/EP2013/052254

(51) Int. Cl.
*G04B 19/32* (2006.01)
*G04B 45/00* (2006.01)
*G04G 9/04* (2006.01)
*G04G 9/00* (2006.01)

(52) U.S. Cl.
CPC ............ *G04B 45/0015* (2013.01); *G04B 19/32* (2013.01); *G04G 9/0041* (2013.01)

(58) Field of Classification Search
CPC ...... G04B 19/30; G04B 19/305; G04B 19/32; G04B 45/0015; G04G 9/0041
USPC ............................ 368/67, 226, 227, 228, 232
See application file for complete search history.

(56) References Cited

U.S. PATENT DOCUMENTS

| | | | | |
|---|---|---|---|---|
| 1,414,628 | A * | 5/1922 | Cuntz | 368/226 |
| 3,431,721 | A * | 3/1969 | Slaugh | 368/226 |
| 6,806,644 | B2 * | 10/2004 | Ueno et al. | 313/512 |
| 7,063,429 | B2 * | 6/2006 | Hirano et al. | 362/23.15 |
| 7,903,503 | B2 * | 3/2011 | Olmes | 368/226 |
| 2013/0200143 | A1 * | 8/2013 | Callegari et al. | 235/375 |
| 2014/0013846 | A1 * | 1/2014 | Decoux et al. | 73/579 |

* cited by examiner

*Primary Examiner* — Vit W Miska
(74) *Attorney, Agent, or Firm* — Greenblum & Bernstein, P.L.C.

(57) ABSTRACT

A timepiece including at least dial, at least one hand mounted on the timepiece and having an upper side and a lower side facing the dial, and a security material arranged on the lower side of the at least one hand. The security material includes a medium containing one or more compounds having luminescent properties in the infrared (IR) range of the electromagnetic spectrum.

44 Claims, 9 Drawing Sheets

METHOD AND SYSTEM FOR AUTHENTICATING A TIMEPIECE

CROSS REFERENCE TO RELATED APPLICATIONS

The present application claims priority to U.S. Provisional Application No. 61/735,785 filed on Dec. 11, 2012, and to International Application No. PCT/EP2013/052254 filed on Feb. 5, 2013, the disclosures of which are expressly incorporated by reference herein in their entireties.

FIELD OF THE INVENTION

The present invention relates to a method and system for authenticating a timepiece, in particular a watch.

BACKGROUND OF THE INVENTION

Counterfeit consumer goods, commonly called knock-offs, are counterfeit or imitation products offered for sale. The spread of counterfeit goods has become global in recent years and the range of goods subject to counterfeiting has increased significantly.

Expensive watches (and spare parts for watches) are vulnerable to counterfeiting, and have been counterfeited for decades. A counterfeit watch is an unauthorized copy of a part or all of an authentic watch. According to estimates by the Swiss Customs Service, there are some 30 to 40 million counterfeit watches put into circulation each year. It is a common cliché that visitors to New York City are approached on the street by vendors with a dozen such counterfeit watches inside their coats, offered at bargain prices. Extremely authentic looking, but very poor quality counterfeit watches with self-winding mechanisms and fully working movements can sell for as little as twenty dollars. The problem is becoming more and more serious, with the quality of the counterfeits constantly increasing. For example, some counterfeits' materials are of remarkably passable quality and may look good to the untrained eye and work well for some years, a possible consequence of increasing competition within the counterfeiting community. Counterfeit watches cause an estimated $1 Billion loss per year to the watch industry.

Authentication solutions that have been used for protection of consumer goods from counterfeiting are often based on marking the item with a specific material, code, or marking, engraving, etc. However, these methods modify the nature and the appearance of the object, and this is often not acceptable in the watch (and other luxury items) industry, where the design of the object and its visual appearance is of paramount importance.

Counterfeiters often focus on the outer appearance of the watch and fit cheaper components inside, because the potential buyer tends to focus more on the outward appearance of the piece. It is, therefore, desirable, when assessing the authenticity of a timepiece, to have as much information as possible. It is furthermore desirable not to have to open the timepiece when checking the authenticity, as the operation requires specialized equipment and procedures, which may impact on the performance and/or integrity of the piece (e.g., water tightness), and which may invalidate the manufacturer's warranty.

It is, therefore, desirable to be able to authenticate a timepiece in a manner that is as non-invasive and as reliable as possible without having to open the timepiece.

SUMMARY OF EMBODIMENTS OF THE INVENTION

An aim of the invention is to provide a method for authenticating a timepiece that is non-invasive and reliable.

This aim is solved by the subject matter of the independent claims. Preferred embodiments are subject matter of the dependent claims.

Aspects of embodiments of the present invention are directed to a timepiece including at least a dial, at least one hand mounted on the timepiece and having an upper side and a lower side facing the dial, and a security material arranged on the lower side of the at least one hand. The security material includes a medium containing one or more compounds having luminescent properties in the infrared (IR) range of the electromagnetic spectrum.

In additional embodiments, the security material has one or more detectable decay time properties.

In further embodiments, the IR range of the electromagnetic spectrum is between approximately 700 to 1600 nm.

In yet additional embodiments, the IR range of the electromagnetic spectrum is between approximately 900 to 1100 nm.

In yet further embodiments, the IR range of the electromagnetic spectrum is between approximately 925 to 990 nm.

In additional embodiments, the medium contains a plurality of different compounds having a respective plurality of different decay time properties.

In further embodiments, the medium contains at least three different compounds having three different decay time properties.

In yet additional embodiments, the one or more compounds are present in the security material with a concentration of 1% to 20% by weight with respect to a total composition.

In yet further embodiments, the one or more compounds are selected from one or more of the group of lanthanide derivatives.

In additional embodiments, the one or more compounds are selected from one or more of Eu and Tb derivatives.

In some embodiments, the derivatives are included in an Yttrium matrix.

In further embodiments, a decay time of the one or more compounds is comprised between approximately 50 µs and 10 ms.

In yet additional embodiments, the dial comprises reflection properties in the IR range of the electromagnetic spectrum.

In yet further embodiments, the reflection properties comprise a reflectivity of more than 10% in the 700 nm to 1500 nm range.

In additional embodiments, an additional layer arranged on the dial that enhances reflectivity properties of the dial in the IR range.

In further embodiments, the additional layer comprises one or more of ITO, an interference pigment, a dielectric multi-layer coating, a cholesteric liquid crystal pigment, and a cholesteric liquid crystal coating.

In yet additional embodiments, the additional layer is invisible to the unaided naked eye.

In yet further embodiments, the additional layer has a specific reflectivity which is correlated with the properties of the security material to validate the combination of the additional layer and the security material.

In additional embodiments, the dial comprises a material to enhance reflectivity properties of the dial in the IR range.

In further embodiments, the security material is configured to produce an emission luminescence upon receiving an excitation light, and a reflection band of the dial overlaps, at least in part, with the wavelength regions of both the excitation light and the emission luminescence.

In yet additional embodiments, at least one of the at least one hand is completely opaque in the wavelength regions of both the excitation light and the emission luminescence.

In yet further embodiments, at least one of the at least one hand is partially transparent or translucent in the wavelength regions of both the excitation light and the emission luminescence.

In additional embodiments, at least one of the at least one hand has one or more holes therein.

Aspects of embodiments of the invention are directed to a process for at least one of reading and validating a timepiece comprising a dial, at least one hand mounted on the timepiece and having an upper side and a lower side facing the dial, and a security material arranged on the lower side of the at least one hand, wherein the security material includes a medium containing one or more compounds having luminescent properties in the infrared (IR) range of the electromagnetic spectrum. The method comprises illuminating the security material for a prescribed amount of time via a reflection on the dial to excite the security material, and measuring a luminescence emitted by the security material, and at least partially reflected by the dial of the timepiece, at two or more different times after the illuminating to determine one or more decay times of the security material and a time-dependence of the luminescence.

In additional embodiments, the validating further comprises comparing the time-dependence of the luminescence with at least one of one or more known reference decay times and one or more luminescence time-dependencies.

In further embodiments, an excitation light of the security material has a prescribed wavelength range.

In yet additional embodiments, the prescribed wavelength is between approximately 925 and 990 nm.

In yet further embodiments, the timepiece additionally includes transparent cover, and wherein the method further comprises projecting the excitation light through the transparent cover.

In additional embodiments, the method further comprises issuing a signal indicating one of authenticity of the timepiece and non-authenticity of the timepiece.

In further embodiments, the signal comprises at least one of: an alert, a hold signal, an alarm, and a notification.

Further aspects of embodiments of the invention are directed to a system for at least one of reading and validating a timepiece comprising a dial, at least one hand mounted on the timepiece and having an upper side and a lower side facing the dial, and a security material arranged on the lower side of the at least one hand, wherein the security material includes a medium containing one or more compounds having luminescent properties in the infrared (IR) range of the electromagnetic spectrum. The method comprises a light for illuminating the security material for a prescribed amount of time via a reflection on the dial to excite the security material, and a detector configured for measuring a luminescence emitted by the security material, and at least partially reflected by the dial of the timepiece, at two or more different times after the illuminating to determine one or more decay times of the security material and a time-dependence of the luminescence.

In additional embodiments, the system further comprises a comparator configured for comparing the time-dependence of the luminescence with at least one of: one or more known reference decay times, and one or more luminescence time-dependencies.

Further aspects of embodiments of the present are directed to a computer readable medium for storing instructions, which, upon being executed by a processor of a computer device, cause the processor to execute a method for at least one of measuring and validating a timepiece comprising a dial, at least one hand mounted on the timepiece and having an upper side and a lower side facing the dial, and a security material arranged on the lower side of the at least one hand, wherein the security material includes a medium containing one or more compounds having luminescent properties in the infrared (IR) range of the electromagnetic spectrum. The method comprises illuminating the security material for a prescribed amount of time via a reflection on the dial to excite the security material, and measuring a luminescence emitted by the security material, and at least partially reflected by the dial of the timepiece, at two or more different times after the illuminating to determine one or more decay times of the security material and a time-dependence of the luminescence.

In further embodiments, the method further comprises comparing the time-dependence of the luminescence with at least one of one or more known reference decay times and one or more luminescence time-dependencies.

Additional aspects of embodiments of the invention are directed to a hand for a timepiece comprising an upper side and a lower side structured and arranged to face a dial of the timepiece, and a security material arranged on the lower side of the hand. The security material includes a medium containing one or more compounds having luminescent properties in the infrared (IR) range of the electromagnetic spectrum.

Further aspects of embodiments of the invention are directed to timepiece comprising a dial, at least one hand mounted on the timepiece and having an upper side and a lower side facing the dial, and a security material arranged on the lower side of the at least one hand. The security material includes a medium containing one or more compounds having luminescent properties in the infrared (IR) range of the electromagnetic spectrum, wherein the security material has one or more detectable decay time properties. The IR range of the electromagnetic spectrum is between approximately 800 to 1500 nm. The one or more compounds are present in the security material with a concentration of 1% to 20% by weight with respect to a total composition. The one or more compounds are selected from one or more of the group of lanthanide derivatives. A decay time of the one or more compounds is between approximately 50 μs and 10 ms. The dial comprises reflection properties in the IR range of the electromagnetic spectrum. The reflection properties comprise a reflectivity of more than 10% in at least part of the 750 nm to 1500 nm range.

In further embodiments, the at least one hand comprises two hands, wherein the two hands comprise different security materials having different luminescent properties.

In additional embodiments, at least some of the excitation light and/or emission light passes through at least one of the one or more partially transparent or translucent hands.

In yet further embodiments, at least some of the excitation light and/or emission light passes through at least one of the one or more holes.

In further embodiments, the signal comprises at least one of a visual and an acoustic signal.

BRIEF DESCRIPTION OF THE FIGURES

For a more complete understanding of the invention, as well as other objects and further features thereof, reference may be had to the following detailed description of the invention in conjunction with the following exemplary and non-limiting drawings wherein.

Reference numbers refer to the same or equivalent parts of the present invention throughout the various figures of the drawings.

DETAILED DESCRIPTION OF EMBODIMENTS OF THE INVENTION

In the following description, the various embodiments of the present invention will be described with respect to the enclosed drawings.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description is taken with the drawings making apparent to those skilled in the art how the forms of the present invention may be embodied in practice. As should be understood, the exemplary representations are not drawn to scale in order to more clearly illustrate aspects of the present invention.

As used herein, the singular foams "a," "an," and "the" include the plural reference unless the context clearly dictates otherwise. For example, reference to "a magnetic material" would also mean that mixtures of one or more magnetic materials can be present unless specifically excluded.

Except where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and claims are approximations that may vary depending upon the desired properties sought to be obtained by the present invention. At the very least, and not to be considered as an attempt to limit the application of the doctrine of equivalents to the scope of the claims, each numerical parameter should be construed in light of the number of significant digits and ordinary rounding conventions.

Additionally, the recitation of numerical ranges within this specification is considered to be a disclosure of all numerical values and ranges within that range. For example, if a range is from about 1 to about 50, it is deemed to include, for example, 1, 7, 34, 23.7, or any other value or range within the range.

The various embodiments disclosed herein can be used separately and in various combinations unless specifically stated to the contrary.

Figure 1:
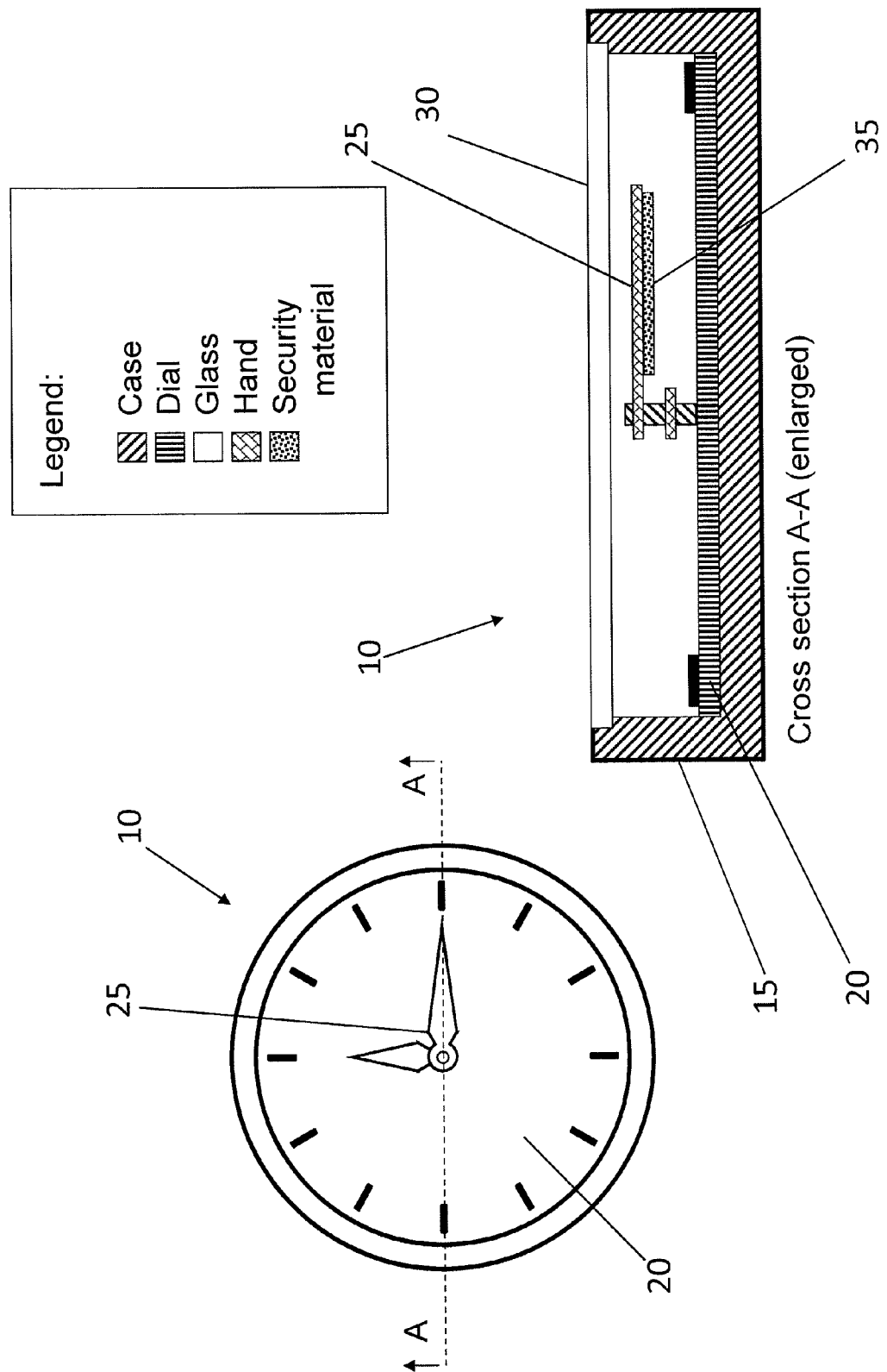
FIG. 1 shows top and sectional schematic representations of a timepiece in accordance with aspects of the present invention.

A timepiece, such as a watch, comprises a case, a dial, one or more hands, and a cover (e.g., a layer of glass or corundum). FIG. 1 shows top and sectional schematic representations of an exemplary timepiece 10 in accordance with aspects of the present invention. As should be understood, the exemplary representation is not drawn to scale in order to more clearly illustrate aspects of the present invention.

As shown in FIG. 1, the timepiece (e.g., watch) 10 comprises a case 15, a dial 20, one or more hands 25, and a cover 30. In accordance with aspects of the present invention, at least one of the hands 25 includes a layer of security material 35 on the backside thereof (i.e., facing the dial 20). In certain embodiments, the security material 35 comprises a medium containing one or more compounds having luminescent (e.g., fluorescent and/or phosphorescent) properties with decay time properties, for example, in the IR range of the electromagnetic spectrum.

In accordance with aspects of the invention, the security material 35 is arranged on the back side of one or more hands 25 so that it does not impact the visual appearance of the watch 10. In some embodiments, at least one of the one or more hands 25 may include holes therein. In accordance with aspects of the invention, the holes in the one or more hands 25 may allow both excitation light and emission light to transmitted more effectively.

According to embodiments of the invention, a watch is subject to an illumination source, and the luminescence of the security material is measured, e.g., once or over a number of intervals. By luminescence, it is intended phosphorescence and/or fluorescence emitted by the security material 35 upon excitation with light. In embodiments, the luminescence of the security material is in the IR range of the electromagnetic spectrum between approximately 700 to 1600 nm, preferably between approximately 900 to 1100 nm, and even more preferably between approximately 925 to 990 nm. A decay time of the one or more compounds, for example, may be between approximately 30 μs and 10 ms. In embodiments, the intervals may be time intervals (e.g., 1 to 10 ms) for measuring luminescence, or may be spectral intervals (e.g., 700-1000 nm).

By implementing aspects of the invention, a watch can be further authenticated (e.g., by make and model) and/or uniquely identified through an analysis and measurement of the specific characteristics of one or more luminescent properties of the security material on the hand the watch. The analysis and measurement may be performed, for example, during or after manufacture of the watch. In embodiments, these specific characteristics of the security material (or, for example, a numerical representation thereof) can be stored in a storage system (e.g., a database) along with an identification number (e.g., a serial number). Subsequently, by performing the analysis and measurement of the specific characteristics of security material, and comparing the measured results with results previously stored in the storage system, the watch can be authenticated. If the measured results match a previously stored identification (or the previously stored identification associated with the identification number of the watch), then the watch is deemed authentic.

While the exemplary embodiment of FIG. 1 illustrates a security material 35 on a portion of the backside of one hand 25, in embodiments, the security material 35 may be arranged on more than one hand 25 (e.g., the minute hand, the hour hand, and/or the second hand). In some embodiments, the security material on each hand may be different. In particular embodiments, the security material 35 may be arranged on an entire underside of a hand 25. As the strength of the emission light is proportional to the amount of security material 35, it may be beneficial to cover the entire underside of the hand with security material 35 so as to increase the detectability of the light emitted by the security material 35. However, the invention contemplates that in some embodiments, the security material 35 may be arranged over less than an entire underside of the hand 25 (e.g., as one or more discrete portions).

In certain contemplated embodiments, the security material 35 may include a plurality of discrete and/or overlapping portions (e.g., of differing compositions), for example, respectively configured to produce a plurality of emission wavelength bands. With additional embodiments, the two materials may be mixed in a single layer, or partially mixed.

In additional embodiments, one or more of the hands 25 may also include a luminescent material on an upper side (i.e., outwardly facing side) of the hand 25, e.g., for aesthetic and/or functional purposes. With such embodiments, the composition of the luminescent material on an upper side may be different from one or more compositions of the security material so that the luminescent properties of the upper and lower sides of the hand may be distinguishable from one another. With other contemplated embodiments, the composition of the luminescent material on an upper side may be the same as one or more compositions of the security material, but, for example, located on different relative radial positions on the hand, so that the luminescent properties of the upper and lower sides of the hand may be distinguishable from one another. In embodiments, the luminescent material on the upper side of the hand may be invisible. In other contemplated embodiments, the luminescent material on the upper side of the hand may be visible, as long as it respects any prescribed esthetic criteria.

The cover 30, for example, may be a layer of glass or corundum, or another sufficiently transparent material. In some contemplated embodiments, the cover 30 may be configured as a filter, e.g., to filter one or more components of the excitation light and/or the emission light. In embodiments, the cover 30 being configured as a filter includes filtering properties of the cover material itself and/or additional layers having filtering properties arranged above and/or below the cover 30. In some embodiments, an entire area of the cover 30 may be configured as a filter. In other contemplated embodiments, portions of the cover 30 less than the entire area may be configured as a filter.

Figure 2:
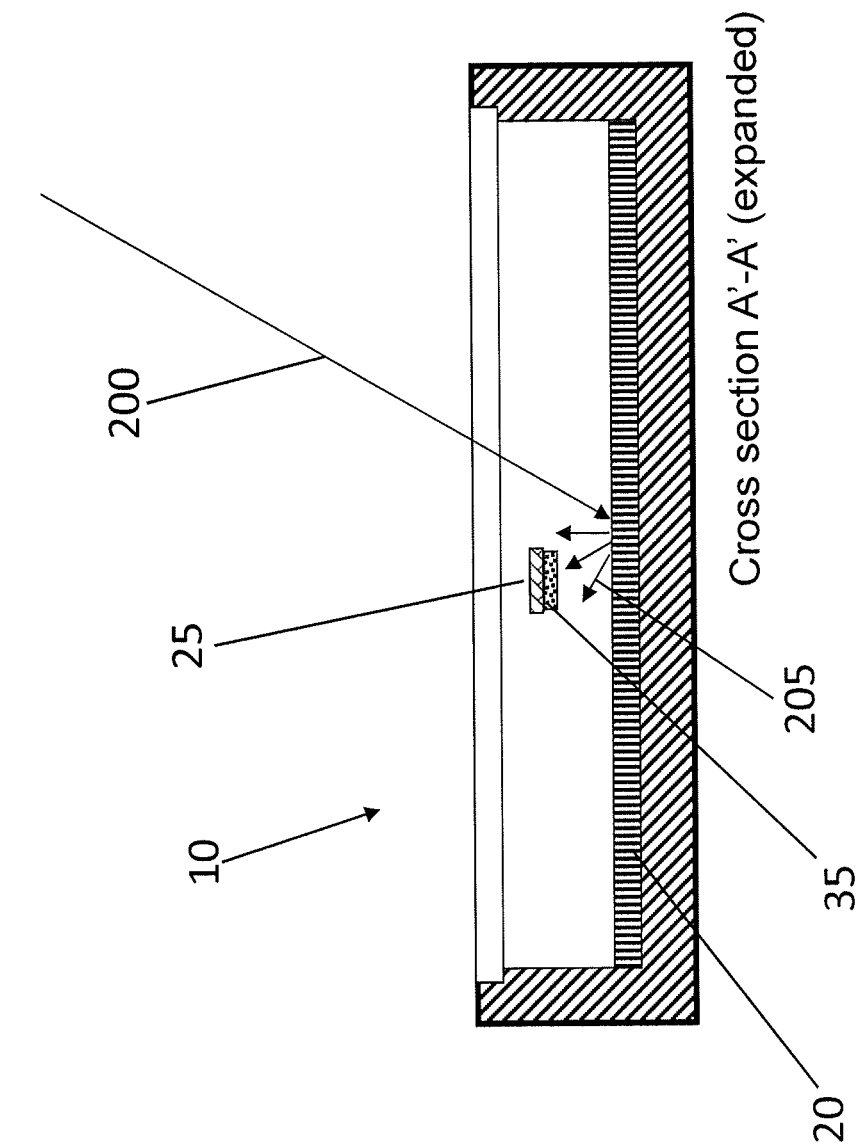
FIG. 2 shows top and sectional schematic representations of a timepiece illustrating an excitation of a security material in accordance with aspects of the present invention.
Figure 2:
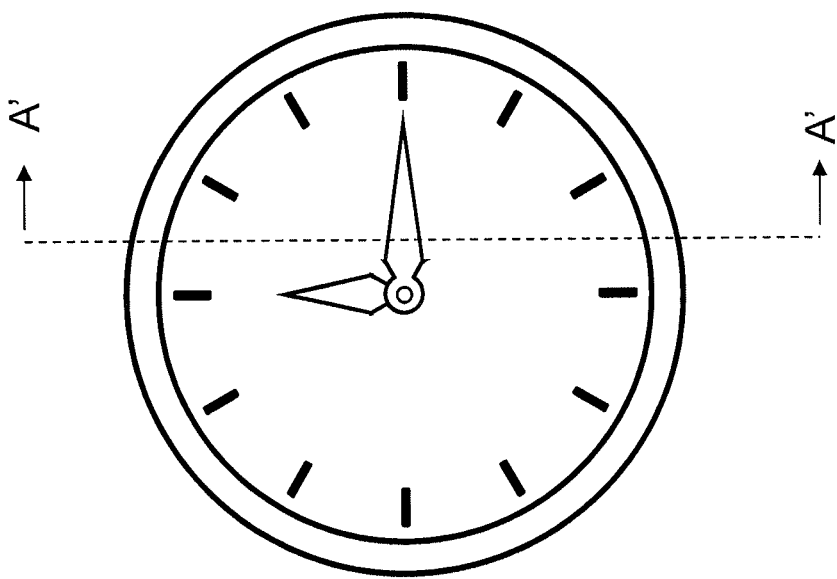

FIG. 2 shows top and sectional schematic representations of the timepiece 10 illustrating an excitation of a security material 35 in accordance with aspects of the present invention. As shown in FIG. 2, a source of excitation light 200 is directed towards the timepiece 10 and is reflected off of the dial 20 (e.g., a white or light colored dial) or portions of the dial 20. The reflected light 205 impacts the security material 35 arranged on the back side of the hand 25 to excite the security material 35.

Figure 3:
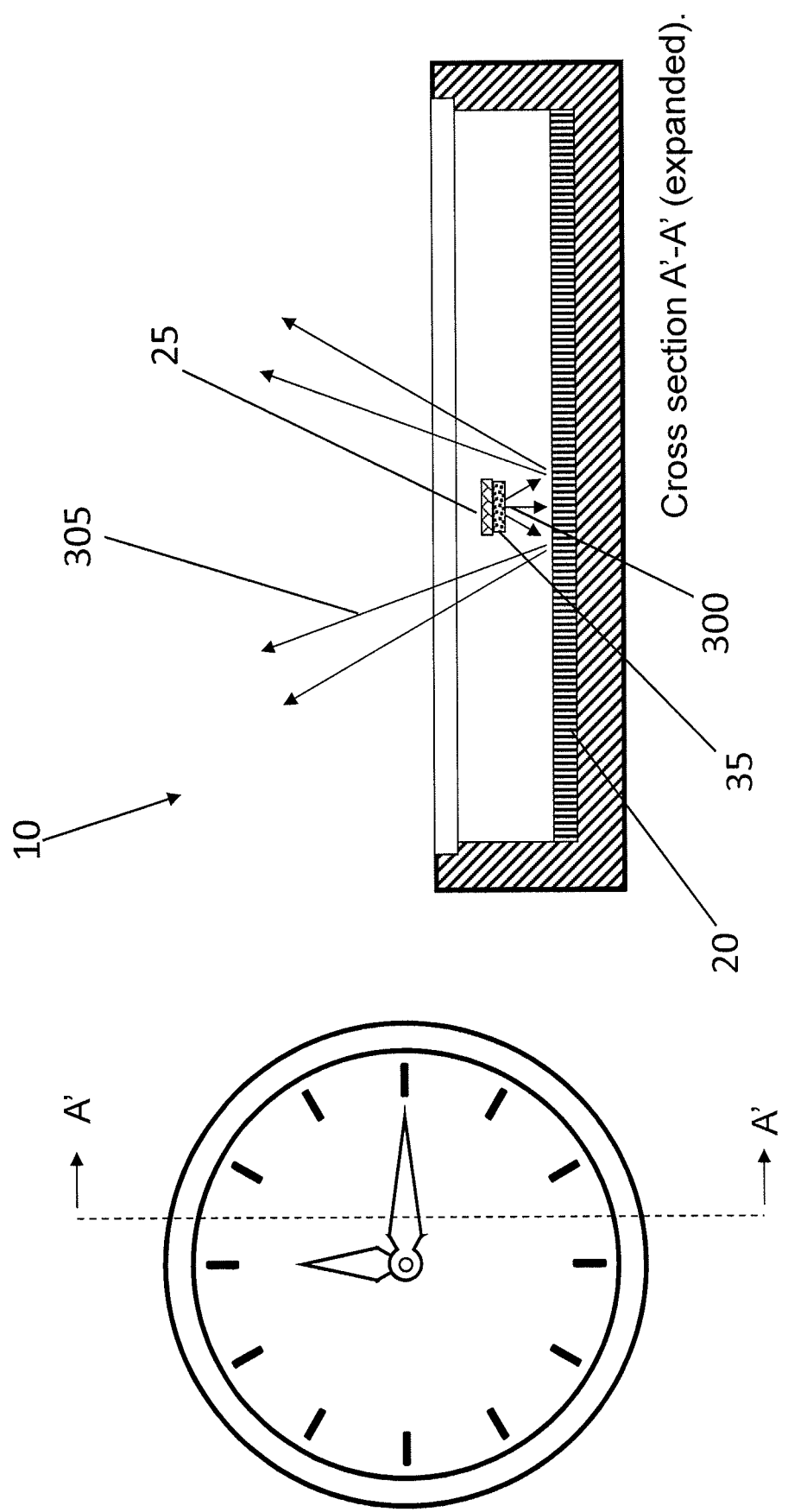
FIG. 3 shows top and sectional schematic representations of a timepiece illustrating an emission of the security material in accordance with aspects of the present invention.

FIG. 3 shows top and sectional schematic representations of the timepiece 10 illustrating an emission of the security material 35 in accordance with aspects of the present invention. As shown in FIG. 3, upon excitation of the security material 35, the security material 35 produces an emission or emitted light 300 (e.g., a fluorescence or phosphorescence). The emitted light 300 is directed at the dial 20, and a reflected emission 305 is at least partially reflected off of the dial 20 and is directed outwardly towards a viewer.

While the exemplary embodiment illustrated in FIGS. 1-3 utilize the dial 20 to reflect the excitation light and the emission light respectively towards and away from the security material 35, the invention contemplates that other surfaces may provide a reflection surface. For example, a top surface of a hand located beneath the hand having the security material arranged on its underside may provide a reflection surface for the excitation and emission light. With additional contemplated embodiments the numerals (and/or the hour markers) on the dial may provide a reflection surface for the excitation and emission light.

Figure 4:
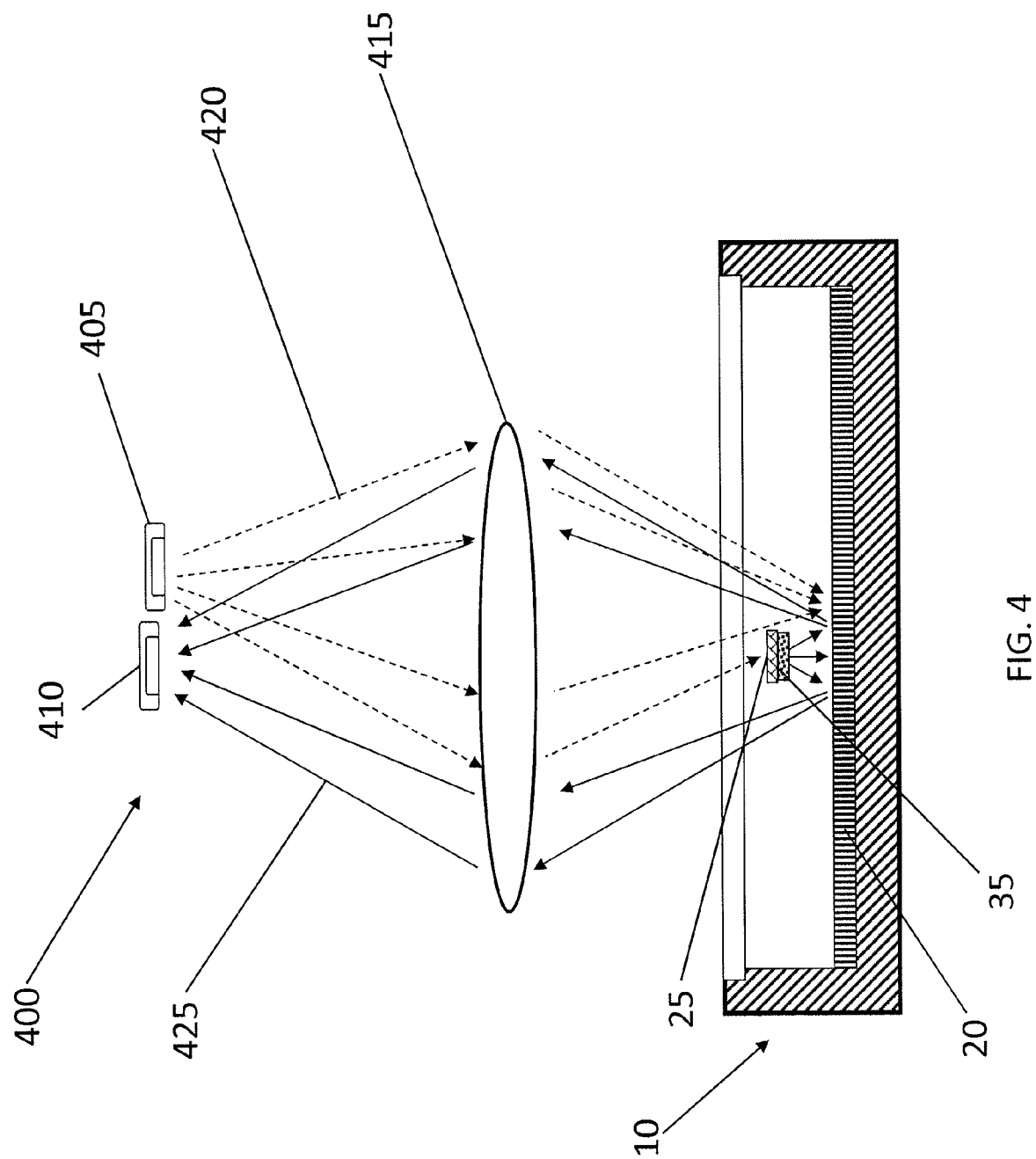
FIG. 4 shows a sectional schematic representation of a timepiece having the security material and a detection system configured for producing an excitation of the security material and a measuring an emission of the security material in accordance with aspects of the present invention.

FIG. 4 shows a sectional schematic representation of a timepiece 10 having the security material 35 and an exemplary detection system 400 configured for producing an excitation of the security material and a measuring an emission of the security material in accordance with aspects of the present invention. As shown in FIG. 4, the detection system 400 includes a light source 405 configured to produce an excitation light 420 (represented with dashed lines). The light source 405 may include on or more filters in order to produce an excitation light 420 with a predetermined wavelength (or range of wavelengths). As shown in FIG. 4, the detection system 400 also includes a lens 415 structured and arranged to focus the excitation light 420 onto the dial 20 of the timepiece 10. As described above, the excitation light 420 is reflected off of the dial 20 and impacts the security material 35 arranged on the back side of the hand 25.

In accordance with aspects of the invention, upon excitation, the security material 35 (e.g., a fluorescent or phosphorescent material) emits an emission light 425 (represented with solid lines). As described above, the excitation light 425 is reflected off of the dial 20 and is directed outwardly away from the timepiece 10. The lens 415 (or, in embodiments, another lens) is structured (or configured) and arranged to focus the emission light 425 towards a detection device 410. In embodiments, the detection device 410 (or reader) may comprise, for example, a fixed device, a handheld device, a mobile phone, and/or a camera, amongst other contemplated detection devices. The detection device 410 may include one or more filters in order to only detect a predetermined wavelength (or range of wavelengths) of the emission light 425.

With an exemplary and non-limiting embodiment, during a time period $T_{exec}$, an illumination source is activated to provide excitation light to the security material of a watch. After a lapse of time, $\Delta T$, the luminescence of the security material is detected and measured by a reader during $T_{det}$. With some embodiments of the present invention, luminescence thresholds may be used when detecting the decay properties of the security material. In additional embodiments a luminescence half life of the security material may be detected and measured to identify properties of the security material.

In accordance with aspects of the invention, the luminescence of the security material may be detected and measured at several intervals. By several intervals, it is intended two or more time intervals, which can be the same or different (e.g., a plurality of different components of the security material luminescence are measured during the same time interval, i.e., simultaneously, or, during different time intervals, i.e., sequentially), overlapping or non-overlapping, have the same duration or different duration, be regularly spaced or not, during which the luminescence is measured.

With an exemplary and non-limiting detection and measurement, the luminescence of the security material is measured at different intervals of, e.g., 0.03 ms in duration from $\Delta T=0$ to $\Delta T=4$ ms to determine a decay profile. In embodiments, measuring the luminescence includes determining spectral characteristics (intensity and/or wavelength) of the luminescence, and/or determining a lifetime (also called decay time) of the luminescence.

Figure 5:
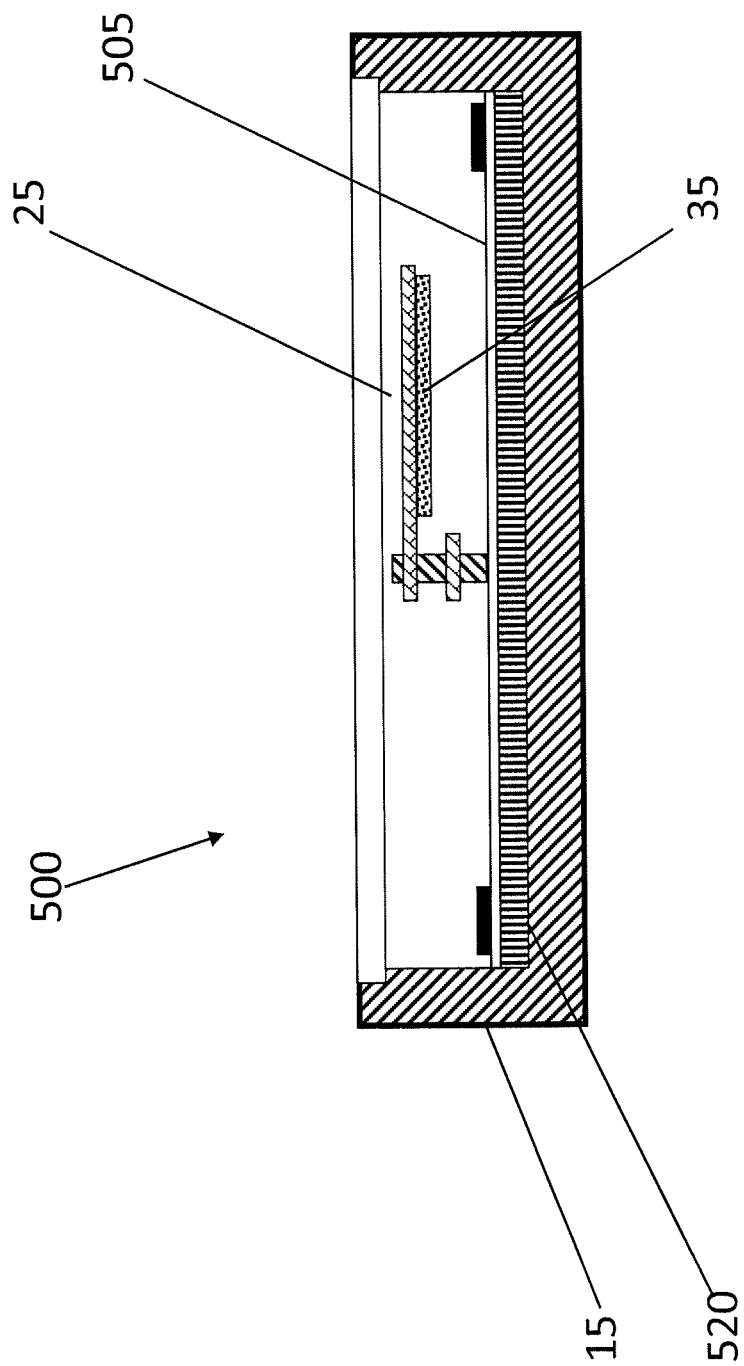
FIG. 5 shows a sectional schematic representation of a timepiece in accordance with aspects of the present invention.

FIG. 5 shows a sectional schematic representation of an exemplary timepiece 50 in accordance with additional aspects of the present invention. While some timepieces include a dial 20 having sufficiently reflective properties (e.g., white or lighter colored), as shown in FIG. 5, the invention contemplates that some dials 520 are black or darker in color, such that they are less reflective. In accordance with aspects of the invention, certain embodiments may include a reflective layer 505 arranged on the dial 520 so that both the excitation light and the emission light are respectively reflected towards and away the security material 35. The reflective layer 505 may be fully reflective in the IR band, while remaining invisible to the unaided (or naked) eye so as not to impact the visual appearance of the timepiece 500. In embodiments, the reflective layer 505 may include one or more reflective materials such as, for example, indium tin oxide (ITO), interference pigments, a dielectric multilayer coating and/or a cholesteric liquid crystal coating, amongst other contemplated materials. In further contemplated embodiments, rather than a discrete reflective layer 505, the dial 520 (e.g., a darker dial) may include one or more materials embedded therein that are configured to enhance the reflectivity of the dial 520 (e.g., in the IR band). In particular embodiments, the embedded materials should remain substantially transparent in the visible range, and hence, substantially invisible to the unaided human eye. However, the invention contemplates other embodiments, in which the embedded materials may be visible to the unaided human eye.

While the exemplary reflective layer 505 is illustrated as covering the entirety of the dial 520, the invention contemplates that the reflective layer 505 may be arranged on less than the entirety of the dial 520.

In accordance with aspects of the invention, one or more hands 20 of a timepiece 10 may include one or more layers of security material 35 so as to impart a signature to the timepiece. In contemplated embodiments, the signature may be unique to the particular timepiece or unique to particular make and model of time piece. Upon manufacture, the signature of the timepiece (e.g., a decay profile comprising one or more decay times of the security material 35) may be measured and stored in a storage system (e.g., a database). Subsequently, in order to validate or authenticate the timepiece 10, the signature (e.g., decay profile) of the timepiece 10 may be measured, for example using the exemplary detection system described above, and compared with the stored signatures (e.g., stored decay profiles) in the database in order to determine the authenticity of the timepiece 10.

The above-described measurements of a particular timepiece should not change over time (i.e., remain stable). For example, as long as components of the watch are not touched or manipulated, the above-described measurements of a particular timepiece will not change. Of course, with maintenance of the time piece (e.g., when the timepiece is opened and the hand is replaced), the above-described measurements may be affected. As such, when timepiece maintenance is performed (e.g., when the timepiece is opened), the timepiece should be recertified (e.g., the decay properties of the security material of the timepiece should be recaptured, and the results of the above-described one or more measurements should be identified and stored).

SYSTEM ENVIRONMENT

As will be appreciated by one skilled in the art, the present invention may be embodied as a timepiece, a system, a method or a computer program product. Accordingly, the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present invention may take the form of a computer program product embodied in any tangible medium of expression having computer-usable program code embodied in the medium.

Any combination of one or more computer usable or computer readable medium(s) may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following:
- an electrical connection having one or more wires,
- a portable computer diskette,
- a hard disk,
- a random access memory (RAM),
- a read-only memory (ROM),
- an erasable programmable read-only memory (EPROM or Flash memory),
- an optical fiber,
- a portable compact disc read-only memory (CDROM),
- an optical storage device,
- a transmission media such as those supporting the Internet or an intranet,
- a magnetic storage device
- a usb key,
- a certificate
- a perforated card, and/or
- a mobile phone.

In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, RF, etc.

Computer program code for carrying out operations of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network. This may include, for example, a local area network (LAN) or a wide area network (WAN), or the connection may be made to an external computer (for example, through the Internet using an Internet Service Provider). Additionally, in embodiments, the present invention may be embodied in a field programmable gate array (FPGA).

Figure 6:
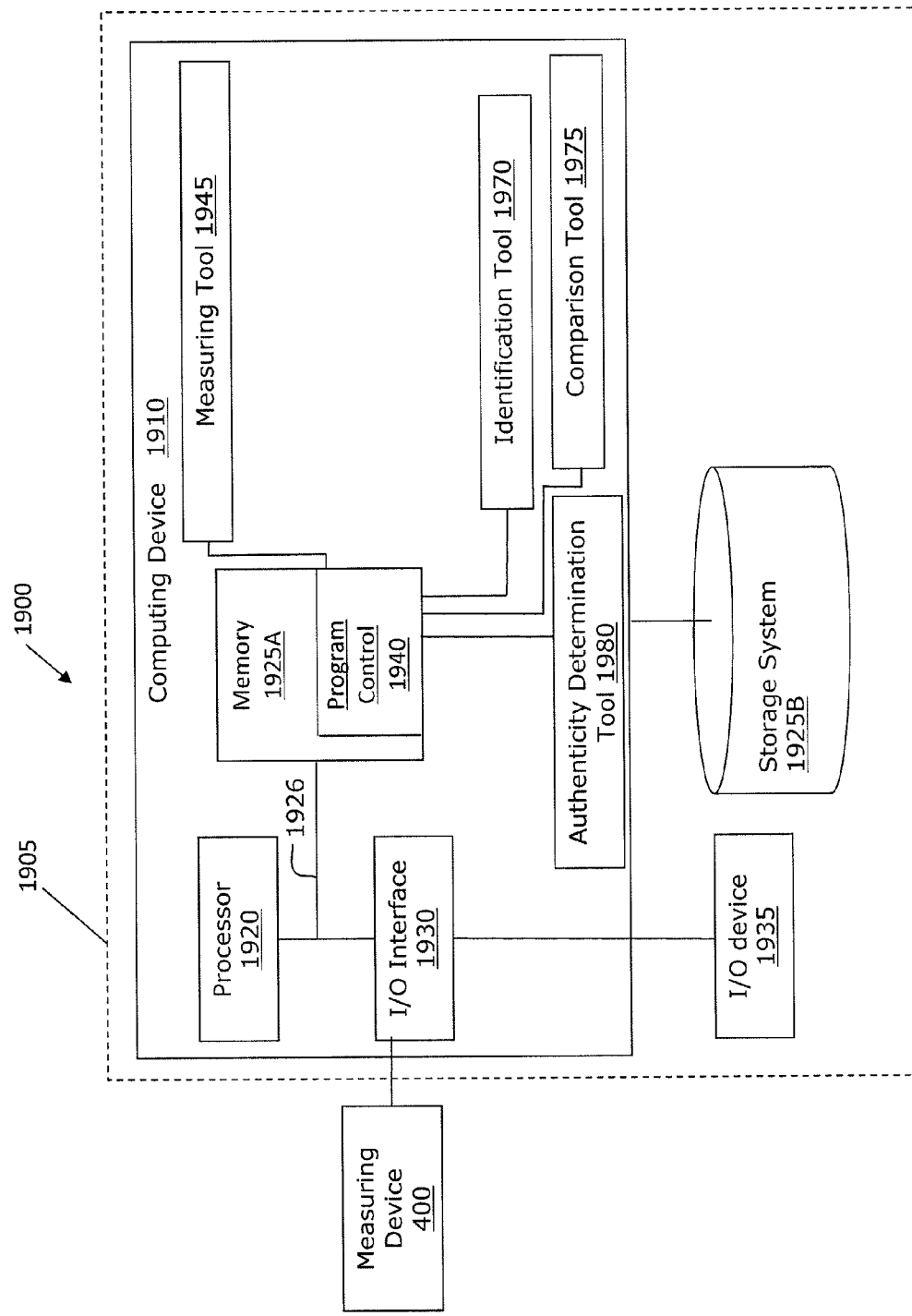
FIG. 6 shows an illustrative environment for managing the processes in accordance with embodiments of the invention.

FIG. 6 shows an illustrative environment 1900 for managing the processes in accordance with the invention. To this extent, the environment 1900 includes a server or other computing system 1905 that can perform the processes described herein. In particular, the server 1905 includes a computing device 1910. The computing device 1910 can be resident on a network infrastructure or computing device of a third party service provider (any of which is generally represented in FIG. 6).

In embodiments, the computing device 1910 includes a measuring tool 1945, an identification tool 1970, a comparison tool 1975, and an authenticity determination tool 1980, which are operable to measure one or more detected decay times of the security material, compare the measured information with stored information, and determine an authenticity of the timepiece, e.g., the processes described herein. The measuring tool 1945, the identification tool 1970, the comparison tool 1975, and the authenticity determination tool 1980 can be implemented as one or more program code in the program control 1940 stored in memory 1925A as separate or combined modules.

The computing device 1910 also includes a processor 1920, memory 1925A, an I/O interface 1930, and a bus 1926. The memory 1925A can include local memory employed during actual execution of program code, bulk storage, and cache memories which provide temporary storage of at least some program code in order to reduce the number of times code must be retrieved from bulk storage during execution. In addition, the computing device includes random access memory (RAM), a read-only memory (ROM), and an operating system (O/S).

The computing device 1910 is in communication with the external I/O device/resource 1935 and the storage system 1925B. For example, the I/O device 1935 can comprise any device that enables an individual to interact with the computing device 1910 or any device that enables the computing device 1910 to communicate with one or more other computing devices using any type of communications link. The external I/O device/resource 1935 may be for example, a handheld device, PDA, handset, keyboard, smartphone, etc. Additionally, in accordance with aspects of the invention, the environment 1900 includes a measuring device 400 for measuring one or more decay times of the security material from one or more timepieces.

In general, the processor 1920 executes computer program code (e.g., program control 1940), which can be stored in the memory 1925A and/or storage system 1925B. Moreover, in accordance with aspects of the invention, the program control 1940 having program code controls the measuring tool 1945, the identification tool 1970, the comparison tool 1975, and the authenticity determination tool 1980. While executing the computer program code, the processor 1920 can read and/or write data to/from memory 1925A, storage system 1925B, and/or I/O interface 1930. The program code executes the processes of the invention. The bus 1926 provides a communications link between each of the components in the computing device 1910.

The computing device 1910 can comprise any general purpose computing article of manufacture capable of executing computer program code installed thereon (e.g., a personal computer, server, etc.). However, it is understood that the computing device 1910 is only representative of various possible equivalent-computing devices that may perform the processes described herein. To this extent, in embodiments, the functionality provided by the computing device 1910 can be implemented by a computing article of manufacture that includes any combination of general and/or specific purpose hardware and/or computer program code. In each embodiment, the program code and hardware can be created using standard programming and engineering techniques, respectively.

Similarly, the computing infrastructure 1905 is only illustrative of various types of computer infrastructures for implementing the invention. For example, in embodiments, the server 1905 comprises two or more computing devices (e.g., a server cluster) that communicate over any type of communications link, such as a network, a shared memory, or the like, to perform the process described herein. Further, while performing the processes described herein, one or more computing devices on the server 1905 can communicate with one or more other computing devices external to the server 1905 using any type of communications link. The communications link can comprise any combination of wired and/or wireless links; any combination of one or more types of networks (e.g., the Internet, a wide area network, a local area network, a virtual private network, etc.); and/or utilize any combination of transmission techniques and protocols.

FLOW DIAGRAMS

Figure 7:
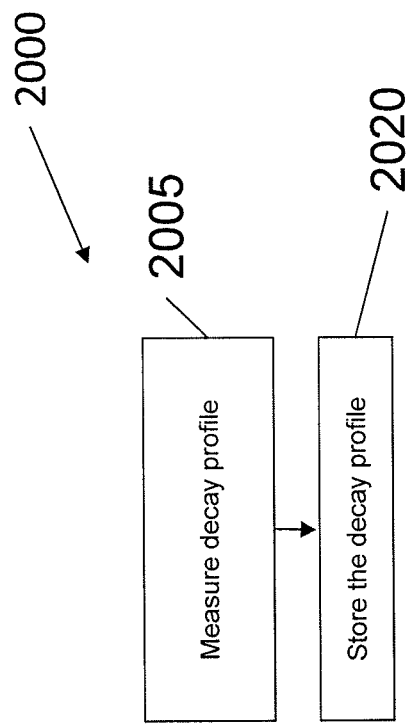
FIGS. 7 and 8 show exemplary flows for performing aspects of embodiments of the present invention.
Figure 8:
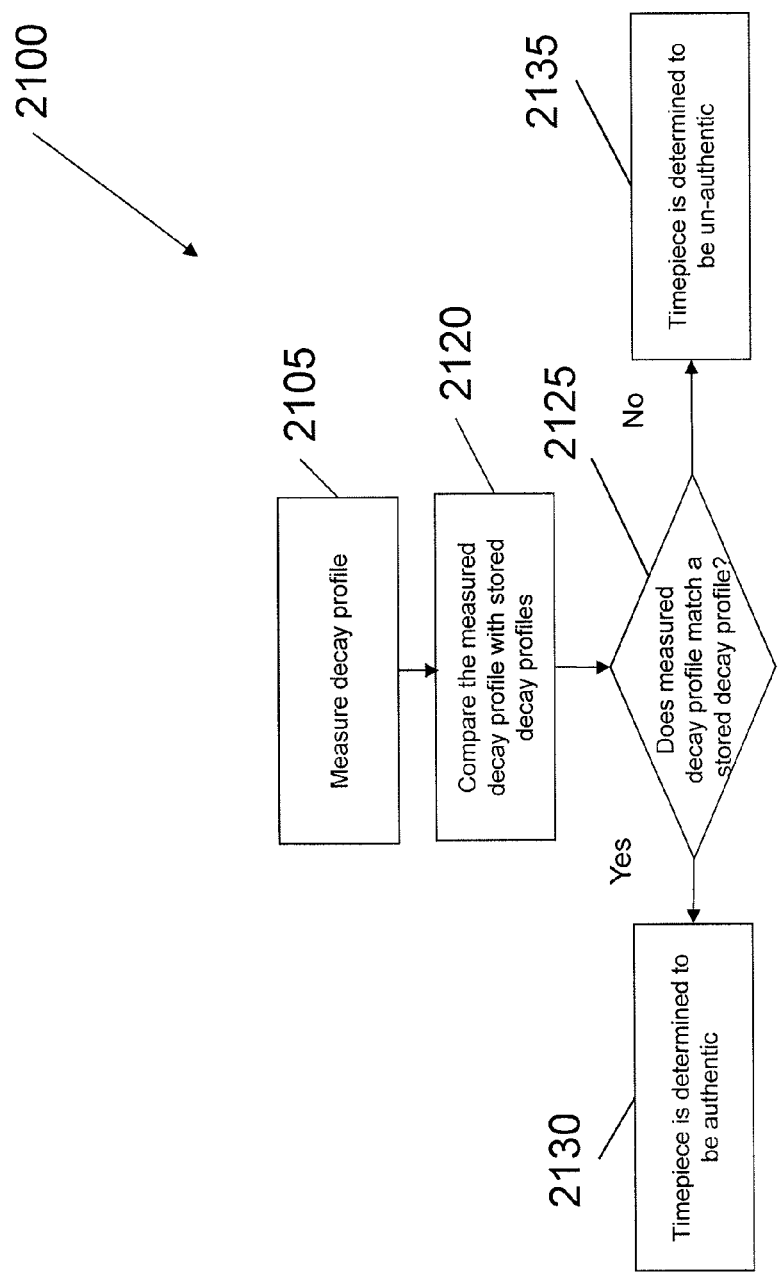

FIGS. 7 and 8 show exemplary flows for performing aspects of the present invention. The steps of FIGS. 7 and 8 may be implemented in the environment of FIG. 6, for example. The flow diagrams may equally represent high-level block diagrams of embodiments of the invention. The flowcharts and/or block diagrams in FIGS. 7 and 8 illustrate the architecture, functionality, and operation of possible implementations of systems, methods and computer program products according to various embodiments of the present invention. In this regard, each block in the flowcharts or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. Each block of each flowchart, and combinations of the flowchart illustrations can be implemented by special purpose hardware-based systems that perform the specified functions or acts, or combinations of special purpose hardware and computer instructions and/or software, as described above. Moreover, the steps of the flow diagrams may be implemented and executed from either a server, in a client server relationship, or they may run on a user workstation with operative information conveyed to the user workstation. In an embodiment, the software elements include firmware, resident software, microcode, etc.

Furthermore, the invention can take the form of a computer program product accessible from a computer-usable or computer-readable medium providing program code for use by or in connection with a computer or any instruction execution system. The software and/or computer program product can be implemented in the environment of FIG. 6. For the purposes of this description, a computer-usable or computer readable medium can be any apparatus that can contain, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable storage medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disc—read/write (CD-R/W) and DVD.

FIG. 7 illustrates an exemplary flow 2000 for creating and storing an identification code for a timepiece. At step 2005, the measuring tool measures a decay profile (e.g., one or more decay times) of a security material. At step 2020, the identification tool stores the decay profile (e.g., the one or more decay times of the security material), for example, as an identification code for the timepiece in a storage system, e.g., a database.

FIG. 8 illustrates an exemplary flow 2100 for authentication and/or identification of a timepiece. As shown in FIG. 8, at step 2105, the measuring tool measures one or more decay times of a security material to determine a decay profile. At step 2120, the comparison tool compares the measured decay profile with one or more stored decay profiles. At step 2125, the authenticity determination tool determines whether the measured decay profile matches a stored decay profile. If, at step 2125, the authenticity determination tool determines that the measured decay profile matches a stored identification code (e.g., stored decay profile of a security material), at step 2130, the timepiece is determined to be authentic. If, at step 2125, the authenticity determination tool determines that the measured decay profile does not match a stored decay profile, at step 2135, the timepiece is determined to be un-authentic.

Figure 9:
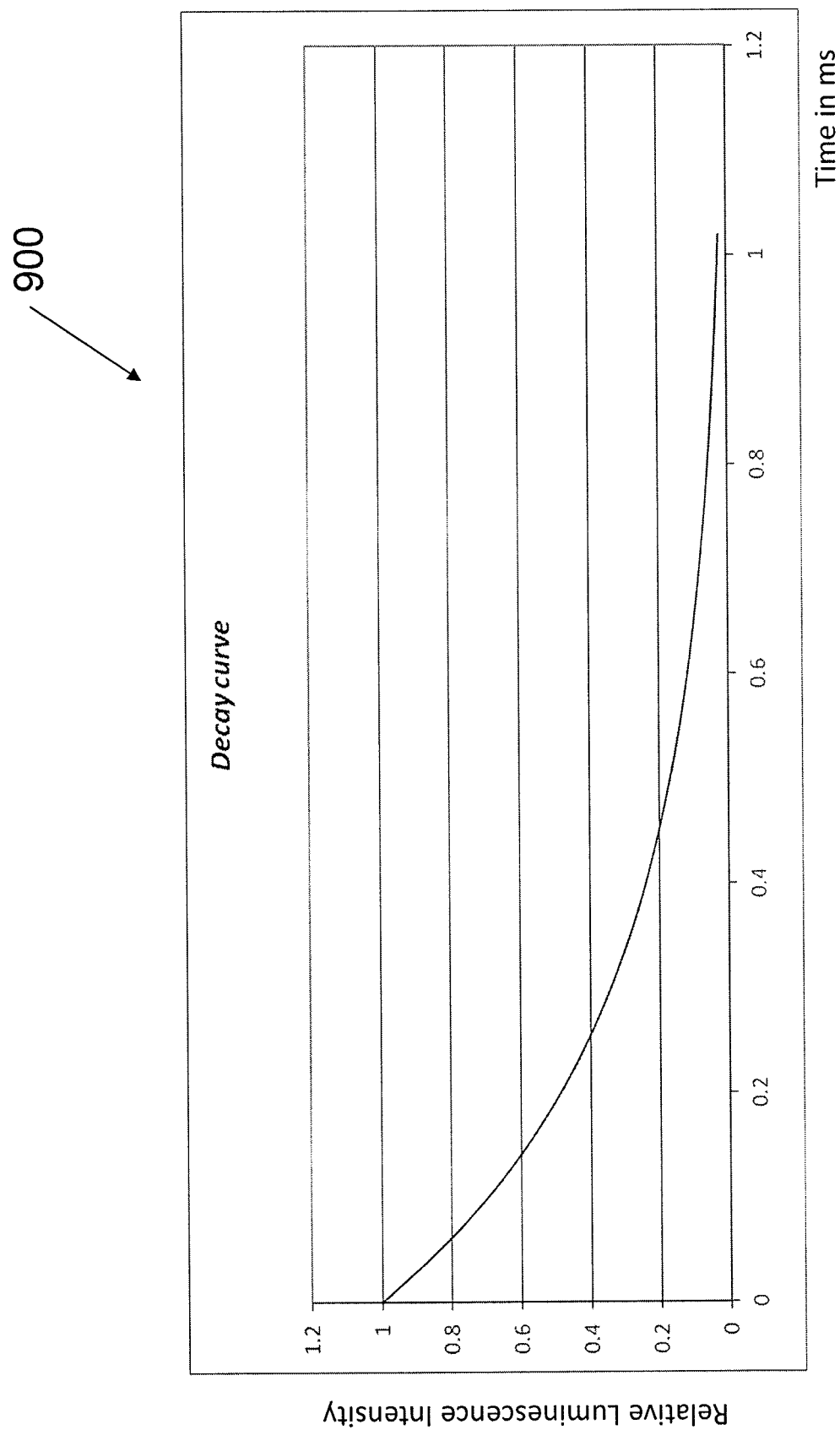
FIG. 9 shows an exemplary decay time curve measured from a hand having a medium containing lanthanides derivatives on one of its faces in accordance with aspects of the present invention.

FIG. 9 shows an exemplary decay time curve 900 measured from a hand having a medium containing lanthanides derivatives on one of its faces in accordance with aspects of the present invention. With the exemplary plot of FIG. 9, the decay time curve 900 is plotted as relative luminescence intensity (e.g., a luminescence normalized to 1) versus time (in milliseconds). In some embodiments, the measure of the decay time curve is obtained by using a measuring device, for example, as described above, to measure the luminescence emitted by the security material and reflected by the dial of the timepiece in accordance with aspects of the invention. As shown in FIG. 9, the relative luminescence of the timepiece decays in a measurable and repeatable manner, such that the measured luminescence decay may serve as an identifier (e.g., a unique identifier) for the timepiece.

While the invention has been described with reference to specific embodiments, those skilled in the art will understand that various changes may be made and equivalents may be substituted for elements thereof without departing from the true spirit and scope of the invention. In addition, modifications may be made without departing from the essential teachings of the invention.

What is claimed is:

1. A timepiece comprising:
   a dial;
   at least one hand mounted on the timepiece and having an upper side and a lower side facing the dial; and
   a security material arranged on the lower side of the at least one hand,
   wherein the security material includes a medium containing one or more compounds having luminescent properties in the infrared (IR) range of the electromagnetic spectrum.

2. The timepiece according to claim 1, wherein the security material has one or more detectable decay time properties.

3. The timepiece according to claim 1, wherein the IR range of the electromagnetic spectrum is between approximately 700 to 1600 nm.

4. The timepiece according to claim 1, wherein the IR range of the electromagnetic spectrum is between approximately 900 to 1100 nm.

5. The timepiece according to claim 1, wherein the IR range of the electromagnetic spectrum is between approximately 925 to 990 nm.

6. The timepiece according to claim 1, wherein the medium contains a plurality of different compounds having a respective plurality of different decay time properties.

7. The timepiece according to claim 1, wherein the medium contains at least three different compounds having three different decay time properties.

8. The timepiece according to claim 1, wherein the one or more compounds are present in the security material with a concentration of 1% to 20% by weight with respect to a total composition.

9. The timepiece according to claim 1, wherein the one or more compounds are selected from one or more of the group of lanthanide derivatives.

10. The timepiece according to claim 9, wherein the one or more compounds are selected from one or more of Eu and Tb derivatives.

11. The timepiece according to claim 10, wherein the one or more of the Eu and Tb derivatives are included in an Yttrium Oxide matrix.

12. The timepiece according to claim 9, wherein the one or more compounds of the group of lanthanide derivatives are included in an Yttrium Oxide matrix.

13. The timepiece according to claim 1, wherein a decay time of the one or more compounds is between approximately 50 μs and 10 ms.

14. The timepiece according to claim 1, wherein the dial comprises reflection properties in the IR range of the electromagnetic spectrum.

15. The timepiece according to claim 14, wherein the reflection properties comprise a reflectivity of more than 10% in at least part of the 750 nm to 1500 nm range.

16. The timepiece according to claim 1, further comprising an additional layer arranged on the dial that enhances reflectivity properties of the dial in the IR range.

17. The timepiece according to claim 16, wherein the additional layer comprises one or more of ITO, an interference pigment, a dielectric multilayer coating, a cholesteric liquid crystal pigment, and a cholesteric liquid crystal coating.

18. The timepiece according to claim 16, wherein the additional layer is invisible to the unaided naked eye.

19. The timepiece according to claim 16, wherein the additional layer has a specific reflectivity which is correlated with the properties of the security material to validate the combination of the additional layer and the security material.

20. The timepiece according to claim 1, wherein the dial comprises a material to enhance reflectivity properties of the dial in the IR range.

21. The timepiece according to claim 1, wherein the security material is configured to produce an emission luminescence upon receiving an excitation light, and a reflection band of the dial overlaps, at least in part, with the wavelength regions of both the excitation light and the emission luminescence.

22. The timepiece according to claim 21, wherein at least one of the at least one hand is completely opaque in the wavelength regions of both the excitation light and the emission luminescence.

23. The timepiece according to claim 21, wherein at least one of the at least one hand is partially transparent or translucent in the wavelength regions of both the excitation light and the emission luminescence.

24. The timepiece according to claim 1, wherein at least one of the at least one hand has one or more holes therein.

25. The timepiece according to claim 1, wherein the dial comprises a material to enhance reflectivity properties of the dial in the IR range.

26. The timepiece according to claim 1, wherein the at least one hand comprises two hands, wherein the two hands comprise different security materials having different luminescent properties.

27. The timepiece according to claim 1, wherein the security material is configured to produce an emission luminescence upon receiving an excitation light, and a reflection band of the dial at least partially overlaps with the wavelength regions of both the excitation light and the emission luminescence.

28. The timepiece according to claim 23, wherein at least some of the excitation light and/or emission light passes through at least one of the one or more partially transparent or translucent hands.

29. The timepiece according to claim 24, wherein at least some of the excitation light and/or emission light passes through at least one of the one or more holes.

30. A method for at least one of reading and validating a timepiece comprising a dial, at least one hand mounted on the timepiece and having an upper side and a lower side facing the dial, and a security material arranged on the lower side of the at least one hand, wherein the security material includes a medium containing one or more compounds having luminescent properties in the infrared (IR) range of the electromagnetic spectrum, the method comprising:
  illuminating the security material for a prescribed amount of time via a reflection on the dial to excite the security material;
  measuring a luminescence emitted by the security material, and at least partially reflected by the dial of the timepiece, at two or more different times after the illuminating to determine one or more decay times of the security material and a time-dependence of the luminescence.

31. The method according to claim 30, wherein the validating further comprises comparing the time-dependence of the luminescence with at least one of one or more known reference decay times and one or more luminescence time-dependencies.

32. The method according to claim 30, wherein an excitation light of the security material has a prescribed wavelength range.

33. The method according to claim 32, wherein the prescribed wavelength is between approximately 925 and 990 nm.

34. The method of claim 30, wherein the timepiece additionally includes transparent cover, and wherein the method further comprises projecting the excitation light through the transparent cover.

35. The method according to claim 30, further comprising issuing a signal indicating one of authenticity of the timepiece and non-authenticity of the timepiece.

36. The method of claim 35, wherein the signal comprises at least one of: an alert, a hold signal, an alarm, and a notification.

37. The method of claim 35, wherein the signal comprises at least one of a visual and an acoustic signal.

38. A system for at least one of reading and validating a timepiece comprising a dial, at least one hand mounted on the timepiece and having an upper side and a lower side facing the dial, and a security material arranged on the lower side of the at least one hand, wherein the security material includes a medium containing one or more compounds having luminescent properties in the infrared (IR) range of the electromagnetic spectrum, the method comprising:
  a light for illuminating the security material for a prescribed amount of time via a reflection on the dial to excite the security material;
  a detector configured for measuring a luminescence emitted by the security material, and at least partially reflected by the dial of the timepiece, at two or more different times after the illuminating to determine one or more decay times of the security material and a time-dependence of the luminescence.

39. The system of claim 38, further comprising a comparator configured for comparing the time-dependence of the luminescence with at least one of:
  one or more known reference decay times, and
  one or more luminescence time-dependencies.

40. A computer readable medium for storing instructions, which, upon being executed by a processor of a computer device, cause the processor to execute a method for at least one of measuring and validating a timepiece comprising a dial, at least one hand mounted on the timepiece and having an upper side and a lower side facing the dial, and a security material arranged on the lower side of the at least one hand, wherein the security material includes a medium containing one or more compounds having luminescent properties in the infrared (IR) range of the electromagnetic spectrum, the method comprising:
  illuminating the security material for a prescribed amount of time via a reflection on the dial to excite the security material;
  measuring a luminescence emitted by the security material, and at least partially reflected by the dial of the timepiece, at two or more different times after the illuminating to determine one or more decay times of the security material and a time-dependence of the luminescence.

41. The computer readable medium of claim 40, wherein the method further comprises comparing the time-dependence of the luminescence with at least one of one or more known reference decay times and one or more luminescence time-dependencies.

42. A hand for a timepiece, comprising:
  an upper side and a lower side structured and arranged to face a dial of the timepiece; and
  a security material arranged on the lower side of the hand, wherein the security material includes a medium containing one or more compounds having luminescent properties in the infrared (IR) range of the electromagnetic spectrum.

43. A timepiece, comprising:
  a dial;
  at least one hand mounted on the timepiece and having an upper side and a lower side facing the dial; and
  a security material arranged on the lower side of the at least one hand, wherein the security material includes a medium containing one or more compounds having luminescent properties in the infrared (IR) range of the electromagnetic spectrum, wherein the security material has one or more detectable decay time properties, wherein the IR range of the electromagnetic spectrum is between approximately 700 to 1600 nm, wherein the one or more compounds are present in the security material with a concentration of 1% to 20% by weight with respect to a total composition, wherein the one or more compounds are selected from one or more of the group of lanthanide derivatives, wherein a decay time of the one or more compounds is between approximately 30 μs and 10 ms, wherein the dial comprises reflection properties in the IR range of the electromagnetic spectrum, and wherein the reflection properties comprise a reflectivity of more than 10% in at least part the 750 nm to 1500 nm range.

44. The timepiece according to claim 43, further comprising an additional layer arranged on the dial that enhances reflectivity properties of the dial in the IR range, wherein the additional layer comprises one or more of ITO, an interference pigment, a dielectric multilayer coating, a cholesteric liquid crystal pigment, and a cholesteric liquid crystal coating, wherein the additional layer is invisible to the unaided naked eye, wherein the additional layer has a specific reflectivity which is correlated with the properties of the security material to validate the combination of the additional layer and the security material.

* * * * *

UNITED STATES PATENT AND TRADEMARK OFFICE
CERTIFICATE OF CORRECTION

| | | |
|---|---|---|
| PATENT NO. | : 9,223,293 B2 | Page 1 of 1 |
| APPLICATION NO. | : 14/103302 | |
| DATED | : December 29, 2015 | |
| INVENTOR(S) | : E. Decoux et al. | |

It is certified that error appears in the above-identified patent and that said Letters Patent is hereby corrected as shown below:

Claims

Column 17, line 18 (claim 43, line 24) please change "part the" to -- part of the --

Signed and Sealed this
Nineteenth Day of April, 2016

Michelle K. Lee
*Director of the United States Patent and Trademark Office*